United States Patent
Tung

(10) Patent No.: US 11,975,071 B2
(45) Date of Patent: May 7, 2024

(54) TUMOR ABLATION USING LOW-INTENSITY ULTRASOUND AND SOUND EXCITABLE DRUG

(71) Applicant: CORNELL UNIVERSITY, Ithaca, NY (US)

(72) Inventor: Ching-Hsuan Tung, New York, NY (US)

(73) Assignee: CORNELL UNIVERSITY, Ithaca, NY (US)

(*) Notice: Subject to any disclaimer, the term of this patent is extended or adjusted under 35 U.S.C. 154(b) by 796 days.

(21) Appl. No.: 17/047,992

(22) PCT Filed: Apr. 16, 2019

(86) PCT No.: PCT/US2019/027624
§ 371 (c)(1),
(2) Date: Oct. 15, 2020

(87) PCT Pub. No.: WO2019/204270
PCT Pub. Date: Oct. 24, 2019

(65) Prior Publication Data
US 2021/0154295 A1 May 27, 2021

Related U.S. Application Data

(60) Provisional application No. 62/658,081, filed on Apr. 16, 2018.

(51) Int. Cl.
*A61K 41/00* (2020.01)
*A61P 35/00* (2006.01)

(52) U.S. Cl.
CPC .......... *A61K 41/0033* (2013.01); *A61P 35/00* (2018.01)

(58) Field of Classification Search
CPC .............. A61K 41/0033; A61P 35/00
See application file for complete search history.

(56) References Cited

U.S. PATENT DOCUMENTS

2006/0097248 A1* 5/2006 Lee .................. B82Y 10/00
549/385

FOREIGN PATENT DOCUMENTS

WO WO-2018191594 A1 * 10/2018

OTHER PUBLICATIONS

Y. Kim et al. Cancer treatment using an optically inert Rose Bengal derivative combined with pulsed focused ultrasound. J Control Release. Dec. 20, 2011;156(3):315-22. doi: 10.1016/j.jconrel.2011.08.016. (Year: 2011).*
L. Feril Jr, et al. Therapeutic potential of low-intensity ultrasound (part 2): biomolecular effects, sonotransfection, and sonopermeabilization. J Med Ultrason (2001). Dec. 2008;35(4):161-7. doi: 10.1007/s10396-008-0195-x. (Year: 2001).*
Y. Yang, et al. Biodegradable Polymer Nanoparticles for Photodynamic Therapy by Bioluminescence Resonance Energy Transfer, Biomacromolecules 2018, vol. 19, IS 1, pp. 201-208, doi: 10.1021/acs.biomac.7b01469. (Year: 2018).*
G. Wan et al. (Recent advances of sonodynamic therapy in cancer treatment. Cancer Biol Med. Sep. 2016;13(3):325-338. doi: 10.20892/j.issn.2095-3941.2016.0068. (Year: 2016).*

(Continued)

*Primary Examiner* — Bahar Craigo
*Assistant Examiner* — Manahil Mirghani Ali AbdalHameed
(74) *Attorney, Agent, or Firm* — Scully, Scott, Murphy & Presser, P.C.

(57) ABSTRACT

A method for ablating cancerous tissue in a subject, the method comprising incorporating a sound excitable compound into said cancerous tissue followed by exposure of said cancerous tissue to low-intensity ultrasound having an intensity of no more than 5 W/cm$^2$, said sound excitable compound having the structure Formula (1) wherein: $X^1$, $X^2$, $X^3$, and $X^4$ are each independently selected from iodine and bromine atoms; $X^5$, $X^6$, $X^7$, and $X^8$ are each independently selected from hydrogen atom, chlorine, bromine, and iodine atoms; $Y^1$ is an —O—, —NR'—, or —CR'$_2$— linker, wherein R' is independently selected from hydrogen atom and methyl; Z is a hydrocarbon linking group containing 1-12 carbon atoms; $R^1$ is selected from hydrogen atom, methyl, —OH, and —OR groups, wherein R is an alkyl group containing one to three carbon atoms; and wherein said Formula (1) includes pharmaceutically acceptable salts and solvates of the compounds embraced by Formula (1).

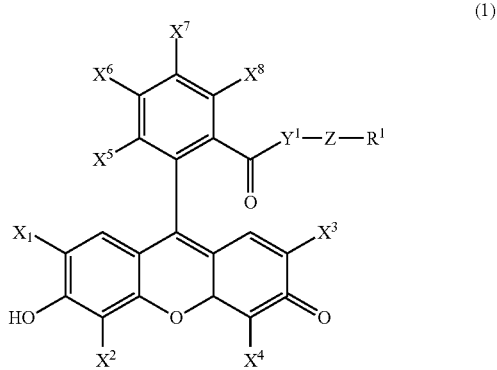

(1)

16 Claims, 8 Drawing Sheets

(56) References Cited

OTHER PUBLICATIONS

Kim Y-S et al., "Cancer Treatment Using an Optically Inert Rose Bengal Derivative Combined With Pulsed Focused Ultrasound", J Control Release 156(3):315-322 (Dec. 20, 2011).
Kuroki M. et al., "Sonodynamic Therapy of Cancer Using Novel Sonosensitizers", Anticancer Research 27:3673-3678 (2007).
Rosenthal I. et al., "Sonodynamic Therapy—A Review of the Synergistic Effects of Drugs and Ultrasound", Ultrasonics Sonochemistry 11:349-363 (2004).
Tung C-H et al., "Tumor Ablation Using Low-Intensity Ultrasound and Sound Excitable Drug", J Control Release 258:67-72 (Jul. 28, 2017).
International Search Report and Written Opinion dated Aug. 5, 2019 received in International Application No. PCT/US2019/27624.

\* cited by examiner

TUMOR ABLATION USING LOW-INTENSITY ULTRASOUND AND SOUND EXCITABLE DRUG

CROSS-REFERENCE TO RELATED APPLICATIONS

Tins application claims the benefit of priority from U.S. Provisional Application No. 62/658,081, filed Apr. 16, 2018, which is herein incorporated by reference in its entirety.

STATEMENT REGARDING FEDERALLY SPONSORED RESEARCH

This invention was made with government support under grant number GM094880 awarded by the National Institutes of Health. The government has certain rights in the invention.

FIELD OF THE INVENTION

This invention generally relates to methods for tumor ablation, and more particularly, such methods that employ ultrasound.

BACKGROUND OF THE INVENTION

Tumor ablation, which generally uses high-energy particles or waves, is an important and conventional means of cancer treatment. Conventional tumor ablation is known to be effective, but is also known to be associated with severe side effects. In particular, the high-energy source causes undesired damage to the tissues along the radiation pathway. In addition, thermal ablation that relies on radiofrequency (RF) energy or high intensity focused ultrasound (HIFU) as the heat source is known to have limitations due to the convective cooling of blood flow, which can protect cancer cells near blood vessels from thermal damage. Thus, a low-energy non-thermal technology that could achieve the same ablation effect without damaging normal tissues would be preferable.

SUMMARY OF THE INVENTION

The present disclosure is directed to methods for ablating tumors using low-energy ultrasound and an excitable drug, as further discussed below. The method is also herein referred to as a sono-membrane rupture therapy (SMRT) method. In the SMRT method, a sound excitable drag (SED) that is non-cytotoxic to cells is herein used to disrupt the plasma membrane under gentle (low energy, i.e., low intensity) ultrasound insonation, typically, no more than 5 W/cm$^2$, e.g., 1 MHz at 1 W/cm$^2$. The frequency and power density of insonation are within the physical therapy and medical imaging windows; thus the applied ultrasound is safe and not harmful to healthy tissues. The insertion of SEDs into the plasma membrane is not toxic to cells; however, the intruding SEDs weaken the membrane's integrity. Under insonation, the ultrasound energy destabilizes the SED-disrupted membranes, which results in membrane rupture and eventual cell death. As further discussed later on in this disclosure, in a xenograft breast tumor model, the SED alone or the ultrasound alone causes little adverse effects to tumor tissue, while the combined treatment triggers necrosis with a brief local insonation of, for example, thirty seconds to three minutes. The described sono-membrane rupture therapy is a safe alternative to conventional high-energy tissue ablation technology, which typically rely on X-rays, gamma rays, electron beams, protons, or high-intensity focused ultrasound.

For purposes of the present invention, the sound excitable compounds are within the scope of the following generic formula:

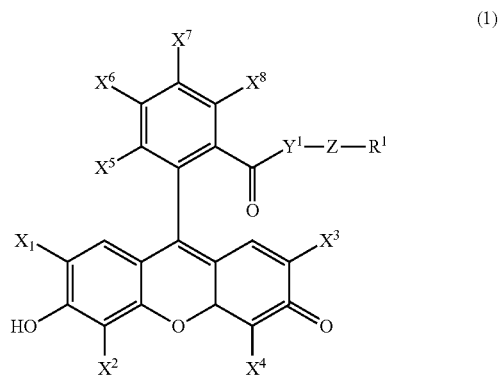

(1)

In Formula (1) above, $X^1$, $X^2$, $X^3$, and $X^4$ are each independently selected from iodine and bromine atoms; $X^5$, $X^6$, $X^7$, and $X^8$ are each independently selected from hydrogen atom, chlorine, bromine, and iodine atoms; $Y^1$ is an —O—, —NR'—, or —CR'$_2$— linker, wherein R' is independently selected from hydrogen atom and methyl; Z is a hydrocarbon linking group containing 1-12 carbon atoms; $R^1$ is selected from hydrogen atom, methyl group, —OH, and —OR groups, wherein R is an alkyl group containing one to three carbon atoms; and wherein Formula (1) includes pharmaceutically acceptable salts, solvates, enantiomers, and physical forms of the compounds embraced by Formula (1).

In some embodiments, the compound being administered is within the scope of the following sub-generic structure:

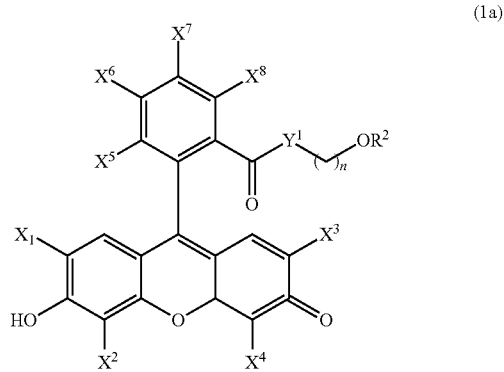

(1a)

In Formula (1a) above, $X^1$, $X^2$, $X^3$, $X^4$, $X^5$, $X^6$, $X^7$, and $X^8$ are defined as above under Formula (1); $Y^1$ is an —O—, —NR'—, or —CR'$_2$— linker, wherein R' is independently selected from hydrogen atom and methyl; $R^2$ is selected from hydrogen atom and alkyl groups containing one to three carbon atoms; and n is an integer of 1-12; and wherein Formula (1a) includes pharmaceutically acceptable salts, solvates, enantiomers, and physical forms of the compounds embraced by Formula (1a).

In further particular embodiments, the compound being administered has the following specific structure, also referred to herein as MI-401:

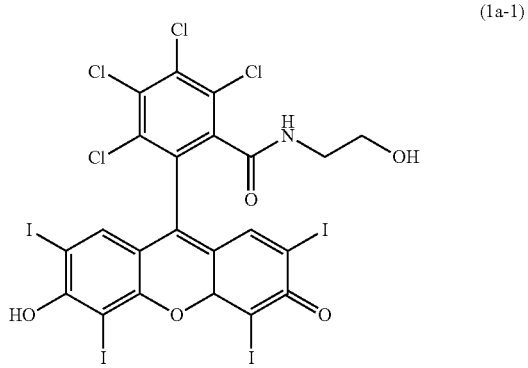

(1a-1)

BRIEF DESCRIPTION OF THE FIGURES

FIG. 2A shows microscopic images after treatment; FIG. 2B is a bar chart showing the results of an MTS viability assay at 24 hours; FIG. 2C show's the results of a FACS analysis after staining with a necrotic indicator, propidium iodide, and an apoptosis indicator, Annexin V, 24 hours after treatment; FIG. 2D is a bar chart showing the ROS scavenger effect. Cells were pretreated with L-histidine, D-mannitol, superoxide dismutase, or N-acetyl cysteine (NAC) and then treated with RB4 (10 μM) for 1 hour and then subjected to insonation (1 MHz, 1 W/cm$^2$, 30 sec). Notably, only NAC was able to rescue a fraction of cells.

FIG. 3A is a graph showing significant growth arrest in the SMRT combination group, which was treated with RB4 (10 μM) and US (1 MHz, 1 W/cm$^2$, 3 min), while the size of tumors of the RB4 alone (10 μM) or US alone (1 MHz, 1 W/cm$^2$, 3 min) control group was about the same as the untreated group. N=7, p<0.0001. FIG. 3B is a representative image of the excised tumors.

FIG. 4A show's HE staining of the tissues. A large necrotic area was found only in the tumor with RB4 and ultrasound combination therapy (panels i & iv). Little effect was found with only ultrasound or RB4 treatment (panels ii & iii). The myocytes maintained their normal structures without damage after RB4 and ultrasound combination therapy (panels v & vi). Original magnification: panels i-iii 4×, panels iv-vi: 20×. Scale bar: panels i-iii 1 mm, panels iv-vi 100 urn. FIG. 4B shows statistical analysis of the necrotic area. The difference between the combination therapy and US alone or RB4 alone is significant (n=5, p<0.0001).

DETAILED DESCRIPTION OF THE INVENTION

Figure 1A:
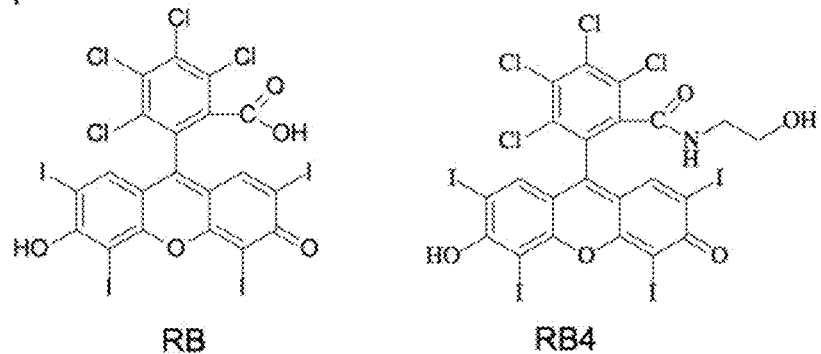
FIG. 1A shows the chemical structures of Rose Bengal (RB) and a derivative thereof (RB4).

The present disclosure is directed to a method for ablating cancerous tissue in a subject. The subject is typically human, although the method should be effective in treating mammals in general. In the method, a sound excitable (xanthene-based) compound (i.e., the SED, as discussed above) is first incorporated into the cancerous tissue. The SED (sound excitable compound) is described in further detail below. For purposes of the invention, the term "incorporated," as used herein, indicates insertion of the sound excitable compound within the cell membrane (also known as "plasma membrane") of cells in the cancerous tissue. The sound excitable compound can be incorporated into the cancerous tissue by, for example, injecting the sound excitable compound directly into the cancerous tissue. After the sound excitable compound is incorporated into the cancerous tissue, the cancerous tissue (with sound excitable compound inserted) is exposed to low-intensity ultrasound. The sound excitable compound is administered in a therapeutically effective amount, which is an amount effective to insert into the cell membrane and later result in cell membrane disruption and cell death when subjected to low-intensity ultrasound.

The term "low-intensity ultrasound" or "low-energy ultrasound," as used herein, refers to ultrasound having an intensity of no more than or less than 5 W/cm$^2$. In different embodiments, the low-intensity ultrasound may have an intensity of no more than or less than, for example, 5, 4.5, 4, 3.5, 3, 2.5, 2, 1.5, 1, or 0.5 W/cm$^2$, or an intensity within a range bounded by any two of the foregoing values. The ultrasound frequency is typically about 0.5, 1, 1.5, 2, 2.5, or 3 MHz or within a range bounded by any two of these values. The cancerous tissue is typically exposed to the low-intensity ultrasound for a continuous period (pulse) of at least 1 second, and more typically, precisely, about, or at least 5, 10, 15, 20, 25, 30, 35, 40, 45, 50, 60, 90, 120, 150, or 180 seconds, or a time within a range bounded by any two of the foregoing values. In some embodiments, any of the foregoing pulses of ultrasound is sufficient to result in the substantial or complete ablation of the tumor. In other embodiments, any of the foregoing pulses of ultrasound is repeated (e.g., twice or more times within one day or over successive days or weeks), along with repeated injections of the sound excitable compound, if necessary, to achieve substantial or complete ablation of the tumor. Any low-intensity ultrasound process suitable for medical administration, as widely known in the art, is applicable herein, such as described in A. K. W, Wood et al., *Ultrasound Med. Biol.,* 41(4):905-928, April 2015, which is herein incorporated by reference in its entirety and which provides ample details on the equipment and conditions typically used in administering low-intensity ultrasound.

The cancerous tissue may be located in any part of the body, such as, for example, the prostate, breast (including triple negative breast cancer), brain, lungs, stomach, intestines, colon, rectum, ovaries, cervix, pancreas, kidney, liver, skin, lymphs, bones, bladder, or uterus. The cancer can also include the presence of one or more carcinomas, sarcomas, lymphomas, blastomas, or teratomas (germ cell tumors).

The xanthene-based sound-excitable compounds considered herein are within the scope of the following generic formula:

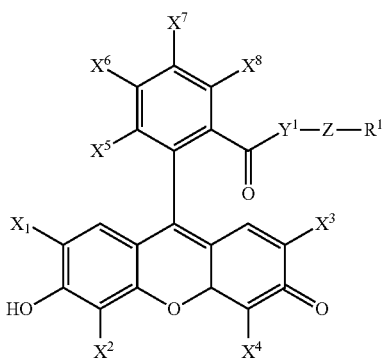

(1)

In Formula (1) above, the variables $X^1$, $X^2$, $X^3$, and $X^4$ are each independently selected from iodine and bromine atoms. In some embodiments, at least one, two, three, or all of $X^1$, $X^2$, $X^3$, and $X^4$ are iodine atoms. In other embodiments, at least one, two, three, or all of $X^1$, $X^2$, $X^3$, and $X^4$ are bromine atoms. The foregoing embodiments include the possibility that one, two, or three of $X^1$, $X^2$, $X^3$, and $X^4$ are iodine atoms while one, two, or three of $X^1$, $X^2$, $X^3$, and $X^4$ are bromine atoms, i.e., where $X^3$, $X^2$, $X^3$, and $X^4$ represent a mix of iodine and bromine atoms.

The variables $X^5$, $X^6$, $X^7$, and $X^8$ are each independently selected from hydrogen atom, chlorine, bromine, and iodine atoms. In some embodiments, $X^5$, $X^6$, $X^7$, and $X^8$ are selected from chlorine, bromine, and iodine atoms. In a first set of embodiments, at least one, two, three, or all of $X^5$, $X^6$, $X^7$, and $X^8$ are hydrogen atoms. In a second set of embodiments, at least one, two, three, or all of $X^5$, $X^6$, $X^7$, and $X^8$ are chlorine atoms. In a third set of embodiments, at least one, two, three, or all of $X^5$, $X^6$, $X^7$, and $X^8$ are bromine atoms, in a fourth set of embodiments, at least one, two, three, or all of $X^5$, $X^6$, $X^7$, and $X^8$ are iodine atoms. The foregoing embodiments include the possibility that one, two, or three of $X^5$, $X^6$, $X^7$, and $X^8$ are hydrogen atoms while one, two, or three of $X^5$, $X^6$, $X^7$, and $X^8$ are chlorine, bromine, and/or iodine atoms, or the possibility that $X^5$, $X^6$, $X^7$, and $X^8$ represent a mix of halide atoms (e.g., chlorine and bromine, or chlorine and iodine, or bromine and iodine, or chlorine, bromine, and iodine).

The variable $Y^1$ is an —O—, —NR'—, or —CR'$_2$— linker, wherein R' is independently selected from hydrogen atom and methyl. When $Y^1$ is —O—, the compounds of Formula (1) contain an ester group (i.e., where —C(O)—$Y^1$—Z—$R^5$ is —C(O)O—Z—$R^1$), When $Y^1$ is —NR'—, the compounds of Formula (1) contain an amide group (i.e., where —C(O)—$Y^1$—Z—$R^1$ is —C(O)NR'—Z—$R^1$). When $Y^1$ is —CR'$_2$—, the compounds of Formula (1) contain a ketone group (i.e., where —C(O)—$Y^1$—Z—$R^1$ is —C(O)CR'$_2$—Z—$R^1$). In the case where $Y^1$ is —CR'$_2$—, $Y^1$ may be —CH$_2$—, —CH(CH$_2$)—, or —C(CH$_3$)$_2$—. In some embodiments, $X^1$, $X^2$, $X^3$, and $X^4$ are iodine atoms and $Y^1$ is an —NR'— linker. In further or alternative embodiments, $X^5$, $X^6$, $X^7$, and $X^8$ are chlorine, bromine, and/or iodine atoms, and $Y^1$ is an —NR'— linker.

The variable Z is a hydrocarbon linking group containing one to twelve (i.e., 1-12) carbon atoms. Z may, in some embodiments, be more particularly defined as having precisely one, two, three, four, five, six, seven, eight, nine, ten, eleven, or twelve carbon atoms, or a particular range of carbon atoms therein, e.g., 1-10, 1-8, 1-6, 1-4, 1-3, 2-12, 2-10, 2-8, 2-6, 2-4, 3-12, 3-10, 3-8, or 3-6 carbon atoms. Z can be saturated or unsaturated, straight-chained (linear) or branched, and either cyclic or acyclic. In some embodiments, Z is composed solely of carbon and hydrogen. The hydrocarbon linking group composed solely of carbon and hydrogen can be, for example, an alkyl, alkenyl, cycloalkyl, cycloalkenyl (aliphatic), or aromatic linking group. The alkyl linkers can be linear or branched. The linear or branched alkyl linkers can be conveniently represented by the formula —(CH$_2$)$_n$—, wherein n is 1-12 or a sub-range therein, and wherein one or more of the shown hydrogen atoms (H) may (optionally) be substituted with a methyl or ethyl group while maintaining 1-12 carbon atoms in Z. The formula —(CH$_2$)$_n$— can also represent an alkenyl linker by replacing two hydrogen atoms on adjacent carbon atoms with a carbon-carbon double bound. In the case of Z being a cyclic hydrocarbon group, the cyclic hydrocarbon group can be conveniently represented by the formula -A-, where A represents a saturated or unsaturated (e.g., aromatic) ring, such as cyclopropyl, cyclobutyl, cyclopentyl, cyclohexyl, cyclopentenyl, cyclopentadienyl, cyclohexenyl, cyclohexadienyl, and phenyl rings.

In some embodiments, Z is a hydrocarbon linker containing 1-12 carbon atoms and at least one heteroatom (i.e., non-carbon and non-hydrogen atom), such as one or more heteroatoms selected from oxygen, nitrogen, sulfur, and halide atoms (e.g., F, Cl, Br, or I atoms). In some embodiments, Z includes one or more ether (—O—) linking groups, hydroxy (OH) groups, carbonyl-containing groups (e.g., ketone, amide, carbamate, or urea functionality), amine, or nitro (NO$_2$) groups. If more than one ether group is present in Z, the group Z may be or include a polyalkyleneoxide (polyalkyleneglycol) moiety, such as a polyethyleneoxide group. In some embodiments, any one or more of the above heteroatoms or heteroatom-containing groups are excluded.

The variable $R^1$ is selected from hydrogen atom (H), methyl, —OH, and —OR groups, wherein R is an alkyl group containing one to three carbon atoms. Some examples of alkyl groups (R) containing one to three carbon atoms include methyl, ethyl, H-propyl, and isopropyl groups. Thus, some examples of alkoxy groups (OR) include methoxy, ethoxy, n-propoxy, and isopropoxy groups. In particular embodiments, $R^1$ is —OH or —OR when Z is a —(CH$_2$)$_n$— linker, wherein n is 1-12 or a sub-range therein, as discussed above. In some embodiments, $X^1$, $X^2$, $X^3$, and $X^4$ are iodine atoms, $Y^1$ is an —NR'— linker, and $R^1$ is —OH. For purposes of the present invention, $R^1$ and Z—$R^1$ do not correspond to carboxylic acid (COOH) groups or salts thereof. In some embodiments, $R^1$ and Z—$R^1$ do not correspond to carboxylic acid esters (C(O)OR).

In some embodiments, the xanthene-based compounds of Formula (1) are within the scope of the following subgeneric formula:

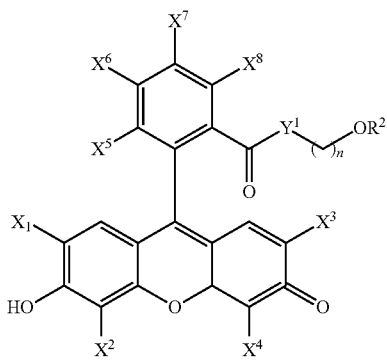

(1a)

In Formula (1a) above, $X^1$, $X^2$, $X^3$, $X^4$, $X^5$, $X^6$, $X^7$, and $X^8$ are defined as above under Formula (1). The variable $Y^1$ is an —O— or —NR'— linker, wherein R' is selected from hydrogen atom and methyl, as described above. The variable $R^2$ is selected from hydrogen atom (H) and alkyl groups containing one to three carbon atoms. The variable n is an integer of 1-12. In particular embodiments, $X^1$, $X^2$, $X^3$, and $X^4$ are iodine atoms. In further particular embodiments, $Y^1$ is an —NR'— linker, wherein R' is selected from hydrogen atom and methyl. In further particular embodiments, $R^2$ is H, In further or alternative embodiments, $X^5$, $X^6$, $X^7$, and $X^8$ are selected from chlorine, bromine, and/or iodine atoms, and $Y^1$ is an —NR'— linker.

The Formulas (1) and (1a) also include pharmaceutically acceptable salts and solvates of the compounds embraced by these formulas. The term "pharmaceutically acceptable salt," as used herein, refers to the relatively non-toxic, inorganic or organic addition salts of compounds of the present invention. A salt form of compounds of Formula (1) or (1a) is possible when the compound contains an amino group, such as when $Y^1$ is an —NR'— linker or in the event Z contains an amine functionality. In that case, a pharmaceutically acceptable salt form can be produced by reaction of the amino-containing compound with a pharmaceutically acceptable acid. These salts can be prepared in situ in the administration vehicle or the dosage form manufacturing process, or by separately reacting a purified compound of the invention in its free base form with a suitable organic or inorganic acid, and isolating the salt formed during subsequent purification. Some representative salts include those generated by reaction of the free base with hydrobromic, hydrochloric, sulfuric, sulfamic, bisulfuric, phosphoric, nitric, acetic, propionic, benzoic, 2-acetoxybenzoic, malic, glycolic, valeric, oleic, palmitic, stearic, lauric, benzoic, lactic, toluenesulfonic, methanesulfonic, ethanedisulfonic, citric, ascorbic, maleic, oxalic, fumaric, phenylacetic, isothionic, succinic, tartaric, glutamic, salicylic, sulfanilic, naphthylic, lactobionic, gluconic, laurylsulfonic acids, and the like. (Berge et al. (1977) "Pharmaceutical Salts", J Pharm. Sci. 66:1-19). As also known in the art, a solvate can be produced by contacting, dissolving, or otherwise treating the active compound with a solvent under conditions where one, two, or more solvent molecules remain associated with each molecule of the active ingredient. When the solvent is or includes water, the solvate may be a hydrate form of the compound. The formulas also encompass all enantiomeric, crystalline, polycrystalline, and amorphous forms of the compounds within the scope of Formulas (1) and (1a).

In some embodiments, the compound being administered has the following specific structure, also referred to herein as MI-401 or RB4 (i.e., 2,3,4,5-tetrachloro-6-(6-hydroxy-2,4,5,7-tetraiodo-3-oxo-3H-xanthen-9-yl)-N-(2-hydroxyethyl)-benzamide):

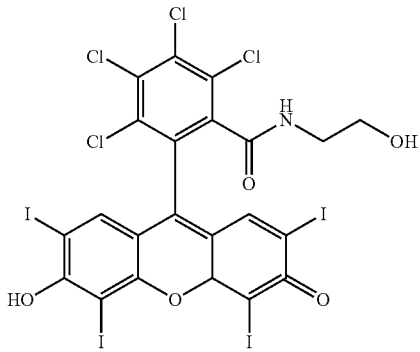

(1a-1)

The above formula for MI-401 (RB-4) also includes all pharmaceutically acceptable salts, solvates, enantiomers, and physical forms, as described above.

The above-described xanthene-based compounds may be synthesized using chemical preparative methods well known in the art, or, in some cases, the compound may be commercially available. The synthesis of some xanthene derivatives, such as Rose Bengal and some of its derivatives, are described in, for example, Y.-S. Kim et al., *Journal of Controlled Release*, 156, pp. 315-322 (2011), which is herein incorporated by reference in its entirety. The synthesis of MI-401 (RB4) is described in C.-H. Tung et al, *Journal of Controlled Release*, 258, pp. 67-72, 2017, which is herein incorporated by reference in its entirely. In particular embodiments, the synthesis of MI-401 involves the following steps: (i) providing 4,5,6,7-tetrachloro-2',4',5',7'-tetraiodofluorescein (508.82 mg, 0.5 mmol) as a first reactant in DMF (3 mL); (ii) providing a N,N-diisopropylethylamine (DIEPA, 2 mL) as a second react; (hi) activating first and second reactants by contact with the coupling agent HBTU (189.62 mg, 0.5 mmol) with stirring at room temperature (RT) for 4 hours; (iv) providing 2-aminoethanol (91 μL, 1.5 mmol) as a third reactant, and reacting the mixture overnight at room temperature; (v) removing solvent under reduced pressure; (vi) extracting the resulting residue with dichloromethane; (vii) washing the residue with brine; (viii) drying the residue over anhydrous sodium sulfate; (ix) concentrating the residue; (x) purifying the residue by a silica gel column; and (xi) eluting the residue with DCM, DCM/MeOH=10/0.5 and 10/1 (v/v).

Generally, the xanthene-based compound according to Formula (1), (1a), or (1a-1) is administered in the form of a liquid pharmaceutical composition wherein the xanthene-based compound is dissolved in a pharmaceutically acceptable carrier (diluent or excipient). The phrase "pharmaceutically acceptable earner" or equivalent term, as used herein, refers to a pharmaceutically acceptable solvent which is, within the scope of sound medical judgment, suitable for use in contact with the tissues of mammals, particularly human beings, without excessive toxicity, irritation, allergic response, or other problem or complication commensurate with a reasonable benefit/risk ratio. In the pharmaceutical composition, the compound is generally dispersed in the physiologically acceptable carrier, by being dissolved or emulsified in a liquid carrier. The carrier should be compatible with the other ingredients of the formulation and physiologically safe to the subject. Any of the carriers known in the art can be suitable herein depending on the mode of administration. Some examples of suitable carriers include water, ethanol, polyols (such as glycerol, propylene glycol, polyethylene glycol, and the like), vegetable oils (such as olive oil), and injectable organic esters (such as ethyl oleate), and suitable mixtures thereof.

The pharmaceutical composition can also include one or more auxiliary agents, such as stabilizers, surfactants, salts, buffering agents, additives, or a combination thereof, all of which are well known in the pharmaceutical arts. Tire stabilizer can be, for example, an oligosaccharide (e.g., sucrose, trehalose, lactose, or a dextran), a sugar alcohol (e.g., mannitol), or a combination thereof. The surfactant can be any suitable surfactant including, for example, those containing polyalkylene oxide units (e.g., Tween 20, Tween 80, Pluronic F-68), which are typically included in amounts of from about 0.001% (w/v) to about 10% (w/v). The salt or buffering agent can be any suitable salt or buffering agent, such as, for example, sodium chloride, or sodium or potassium phosphate, respectively. Some examples of additives include, for example, glycerol, benzyl alcohol, and 1,1,1-trichloro-2-methyl-2-propanol (e.g., chloretone or chlorobutanol). If required, the pH of the solutions can be suitably adjusted by inclusion of a pH adjusting agent. Pharmaceutical compositions and formulations for topical administration may include transdermal patches, ointments, lotions, creams, gels, drops, sprays, and liquids. The pharmaceutical formulation may be in the form of a sterile aqueous solution that contains one or more buffers, diluents, and/or other suitable additives such as, but not limited to, penetration enhancers and carrier compounds.

The xanthene-based compound of Formula (1) or sub-formula is administered in a therapeutically effective amount. The therapeutically effective amount is an amount effective for the xanthene-based compound to insert into the cell membrane and later result in cell membrane disruption and cell death when subjected to low-intensity ultrasound. The effective amount is generally determined by the physician on a case-by-case basis. Several factors are typically taken into account when determining an appropriate dosage to achieve an effective amount. These factors may include the condition being treated and the severity of the condition. The dosage may be expressed in terms of a concentration of the compound in bodily tissue, typically about 1, 2, 5, 10, 20, 30, 40, or 50 µM, or a concentration within a range bounded by any two of the foregoing values. Typically, the xanthene-based compound, described above, is injected directly into or within the vicinity of bodily tissue where the cancerous tissue (tumor) is present. A typical regimen is an injection, in any of the dosage levels provided above, once or twice a day, or once every two or three days, or once a week, for at least two, three, four, five, or six weeks, along with exposure to ultrasound according to an equivalent regimen.

In other embodiments, particularly where the cancerous tissue is on or close to the skin, the xanthene-based compound may be administered via a patch placed on the skin. Administration via a patch is highly advantageous since this eliminates the need for a patient to receive repetitive multi-needle injections. The patch beneficially provides a localized convenient and painless administration method. In particular embodiments, the patch is based on a transdermal micro-size needle array device. A degradable microneedle patch containing a drag-loaded and cross-linked matrix for sustained drug delivery into subcutaneous tissues can be used. Such a patch is described in G. Kogan, et al., *Biotechnol Lett* 2007, 29, 17, the contents of which are herein incorporated by reference.

The microneedle patch can be prepared, for example, on a uniform silicone mold. In a particular embodiment, the microneedle array contains 121 needles in a 7×7 $mm^2$ patch with a center-to-center interval of 600 µm. Each microneedle may be of a conical shape, such as 300 µm in diameter at the base and 800 µm in height. The drugs may be embedded into a methylated hyaluronic acid (HA) polymer crosslinked with N,N'-methylenebis (acrylamide) under UV light (365 nm) (e.g., Kogan et al, supra; and Y. Zhang et al., *ACS Nano*, 11, 9223, 2017), The cross-linked HA-based matrix can enhance the stiffness of the microneedle for efficient penetration through the skin as well as enable sustained release of drug from the tips, which helps maintain local constitutive high drag concentrations in cancerous tissues.

Examples have been set forth below for the purpose of illustration and to describe the best mode of the invention at the present time. However, the scope of this invention is not to be in any way limited by the examples set forth herein.

EXAMPLES

The following experiments employed RB4, a novel synthetic xanthene analog having the chemical structure shown in FIG. 1A. FIG. 1A also shows the structure of RB (Rose Bengal), a precursor for producing RB4.

Synthesis of RB4 (2,3,4,5-tetrachloro-6-(6-hydroxy-2,4,5,7-tetraiodo-3-oxo-3H-xanthen-9-yl)-N-(2-hydroxyethyl)-benzamide)

To a solution of Rose Bengal (509 mg, 0.5 mmol) in DMF (3 mL) and DIEPA (2 ml) was added HBTU (190 mg, 0.5 mmol). The solution was stirred at room temperature (RT) for 4 hours, then 2-aminoethanol (91 µL, 1.5 mmol) was added and reacted overnight at RT. The solvent was removed under reduced pressure. The residue was extracted with dichloromethane (DCM), washed with brine, dried over anhydrous sodium sulfate, and concentrated. The residue was purified by silica gel column, eluted with DCM, DCM/MeOH=10/0.5 and 10/1 (V/V) to yield a pale yellow solid product (161 mg, yield 31.7%). TCL: $R_f$=0.3, DCM/MeOH=10/1. $^1$H NMR (DMSO-d6, 300 MHz): δ 2.99 (s, 2H), 3.32 (s, 2H), 4.60 (br, 1H), 5.76 (s, 1H), 7.25 (s, 1H), 10.07 (s, 1H). LRESI-MS: 1015.57 (M-H)$^-$.

Tumor Cell Culture and Animals

MDA-MB-468 cells (breast cancer cell line) were obtained from the American Type Culture Collection and were maintained in Leibovitz's L-15 medium, and supplemented with 10% fetal bovine serum and antibiotics penicillin (100 µg/mL) and streptomycin (100 µg/mL) without $CO_2$. HT1080-Luc2 ceils were grown at 37° C. with 5% $CO_2$ in Eagle's MEM, and supplemented with 10% fetal bovine serum and antibiotics penicillin (100 µg/mL) and streptomycin (100 µg/mL). All animal studies were performed in compliance with the approved animal protocols and guidelines of the Institutional Animal Care and Use Committee of Weill Cornell Medicine.

Ultrasound system: A portable bench top ultrasound system with 1-3 MHz, and 10, 20, 50 and 100% duty cycle capability was used to conduct all studies. Transducer one (5 $cm^2$, Model #901150, Metron) and transducer two (0.75 $cm^2$, Model #901175, Metron) were used in the cell culture and animal studies, respectively.

Sonotoxicity with RB4: MDA-MB-468 cells (5×10$^4$) in 24 well plates were incubated in complete media with 10 μM RB4 for 1 hour prior to the ultrasound treatment. The plates were then placed on a pre-cut gel pad (2 cm×3 cm) with multipurpose ultrasound gel over a mounted handheld ultrasound transducer (5 cm$^2$) at 1 MHz, 1 W/cm$^2$ for 30 s, 100% DC. Cells were checked under an EVOS® FL Auto Cell Imaging system microscope. Cell viability at 24 hours was quantitated using an MTS assay. The plate was incubated at 37° C. for 4 hours. Absorbance was measured at 490 nm using a microplate reader.

Mechanistic study of death process by flow cytometry: MDA-MB-468 cells (5×10$^4$) were incubated in complete media with or without 10 μM RB4 for 1 hour prior to ultrasound treatment. Then the plates were insonated at 1 MHz, 1 W/cm$^2$, 30 sec, 100% duty cycle. Following treatment, cells were re-incubated for 1 day, 4 groups of cells (Control, RB4 alone, ultrasound alone, and RB4 combined with ultrasound) were collected and washed twice with pre-cooled PBS. Cells were stained with FITC-conjugated Annexin-Y and propidium iodide for 15 minutes as per the manufacture's instructions, and then analyzed by flow cytometry. The percentage of dead cells and those undergoing apoptosis were analyzed using flow 'cytometry' analysis software.

Chemical ROS assay: To study the insonation induced ROS generation in solution, RB4 was tested using a modified 2', 7'-dichlorofluorescin diacetate (DCFH-DA) assay. DCFH-DA (1 ml, 1 mM in MeOH) was hydrolyzed in NaOH aqueous solution (0.01N, 4 mL) at RT for 30 minutes to yield anon-fluorescent DCFH intermediate. The solution was neutralized with 20 mL of NaH$_2$PO$_4$ (25 mM) and shielded with aluminum foil. The final solution of DCFH was around 40 μM. RB4 (1.0 mg) was dissolved in DMSO (1 mL) and then diluted with water into a 20 μM solution. The RB4 solution (20 μM, 10 mL) was mixed with a DCFH solution (40 μM, 10 mL) as the test solution. The test solution (0.5 mL) was placed into each well of a 24-well plate. The DCFH solution without RB4 was included as a background control. The plates were treated with ultrasound (0.4-1.2 watt/cm$^2$) one well by one well for 30 seconds: and the insonated wells were then checked using a fluorescence plate reader, ex 485 nm/em 520 nm.

Cell based ROS scavenging assay: MDA-MB-468 cells (5×10$^4$) were treated with free radical scavengers, L-histidine (10 mM), D-mannitol (100 mM), N-acetyl cysteine (NAC, 0.5 mM), and superoxide dismutase (SOD, 100 μg/mL) for 30 minutes. The treated cells were then incubated with fresh media containing RB4 (10 μM) for an hour. After incubation, the wells were insonated (1 MHz, 1 W/cm$^2$, 30 sec, 100% DC) as described above. One day later, the cell's viability was assessed using the MTS solution.

In vivo sono-membrane rupture therapy (SMRT) effect using preloaded tumor cells: MDA-MB-468 cells were suspended in PBS or RB4 (10 μM) in PBS for 1 day. The cells (5×10$^6$, 0.1 mL) were subcutaneously injected into both flanks. The left tumors, which were only treated with PBS, were the internal control; while the right tumors were treated with RB4 (10 μM) only, ultrasound only (1 MHz, 1 W/cm$^2$, 100% DC, 3 minutes), or an RB4-ultrasound combination (n=7). The transducer size was 0.75 cm$^2$. Tumor size was measured with slide calipers on days 7,10, 14,17, 21,24, 28, and 36.

In vivo SMRT effect with intra-tumoral injected RB4: MDA-MB-468 cells (10$^7$, 0.1 mL PBS) were subcutaneously inoculated into both flanks of BALB/c Nu/Nu female nude mice (5-6 weeks). The RB4 injections and ultrasound therapies were performed when the tumors had grown to approximately 4-5 mm in diameter, 20-22 days after inoculation. The tumors were treated with RB4 (10 μM, 50 μl) only, ultrasound only (1 MHz, 1 W cm2, 100% DC, 3 minutes), and a RB4-ultrasound combination (n=5), Under isoflurane anesthesia, RB4 was directly injected to the tumors of the mice. The ultrasound treatment was then performed immediately after the injection of RB4, with same transducer size. The same RB4-ultrasound treatment was performed on the thigh muscles of the mice.

Histochemical analysis: Tumors and muscle tissue were harvested 2 days after therapy and the specimens were fixed in 10% formalin, cut in half, and embedded in paraffin. The paraffin sections (7 μm thick) were stained with hematoxylin-eosin (H&E). ImageJ 1.48 was used to measure the size of whole tumor and necrotic areas in the tumors.

Statistics: The measurement was performed three times for each group by an experienced pathologist. Statistical analysis was performed with one and two-way ANOVA, followed by Bonferroni's multiple comparison tests using statistical software, p values less trial's 0.05 were considered statistically significant.

Results and Discussion

Rose Bengal (RB, FIG. 1A), a known photosensitizer, has previously been used in photodynamic therapy. Interestingly, it is known that at a very high concentration (>100 μM) and under ultrasound insonation, RB can generate lethal reactive oxygen species (ROS) to kill cells in vitro and potentially in vivo. It is believed that the inertial cavitation process, induced by the ultrasound, triggers sono-luminescence and pyrolysis. The associated light reacted with the photosensitive RB, resulting in ROS dependent cytotoxicity. Therefore, RB has been proposed as a sonosensitizer.

Figure 1B:
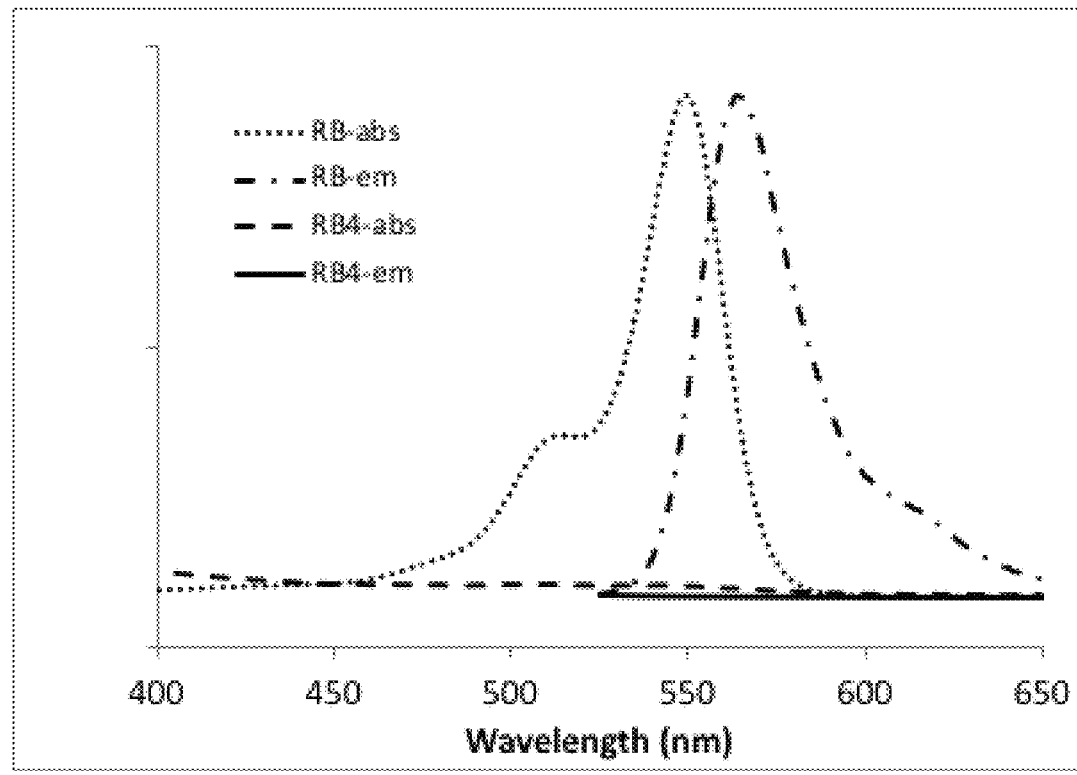
FIG. 1B shows the absorption (ABS) and emission (EM) spectra of RB and RB4.

Among the tested molecules, an RB derivative, RB4 (2,3,4,5-tetrachloro-6-(6-hydroxy-2,4,5,7-tetraiodo-3-oxo-3H-xanthen-9-yl)-N-(2-hydroxyethyl)-benzamide), as shown in FIG. 1A, was herein identified to be non-photosensitive and to have a cell killing capability when exposed to low-intensity ultrasound. The parent molecule, RB, has absorption and emission maximum of 549 nm and 565 nm, respectively, while RB4, the N-2-hydroxyethyl amidated derivative, has neither absorption nor emission above 400 nm (FIG. 1B).

Figure 2A:
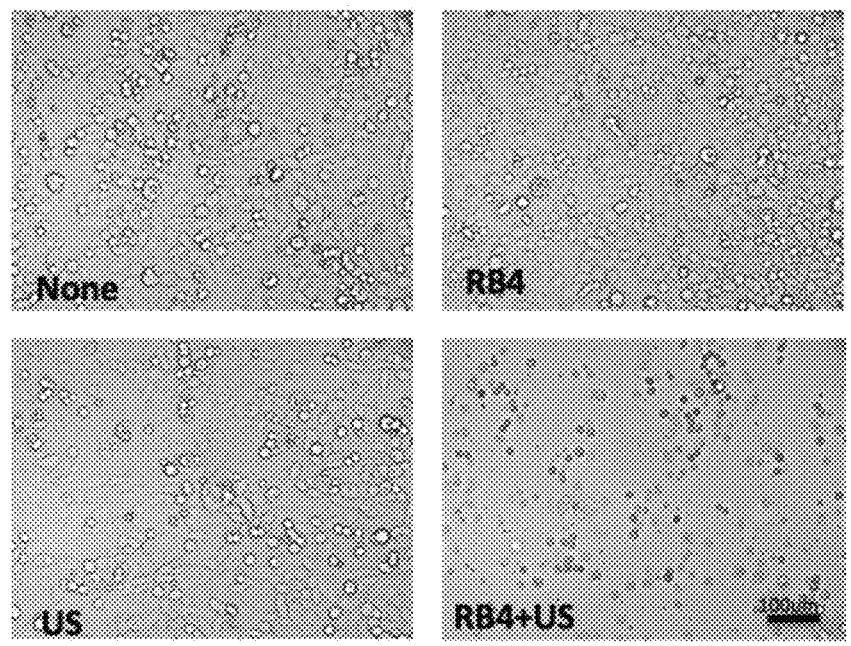
FIGS. 2A-2D show the in vitro SMRT effect. MDA-MB468 breast cancer cells were treated with RB4 (10 μM) and US (1 MHz, 1 W/cm$^2$, 30 sec), RB4 alone (10 μM), US alone (1 MHz, 1 W/cm$^2$, 30 sec), or none, where "US"=ultrasound.
Figure 2B:
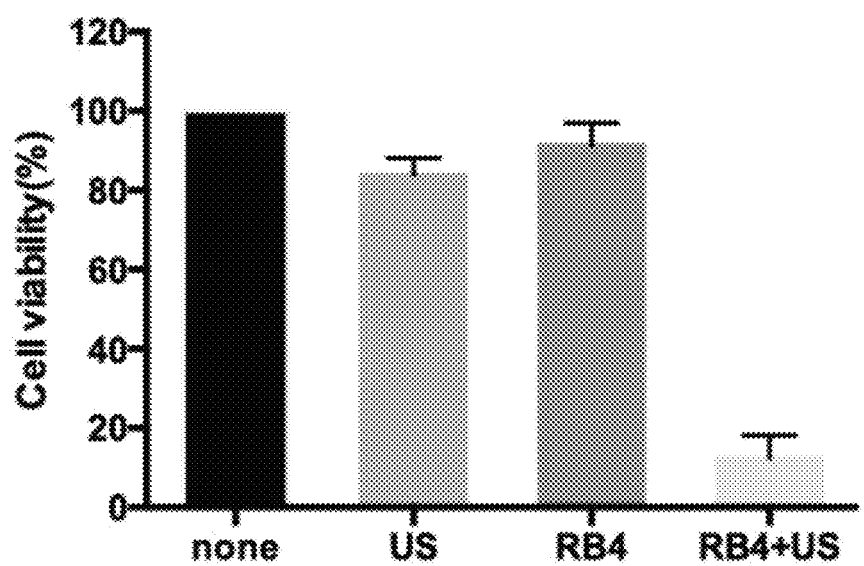

RB4's sound sensitivity was validated with triple negative breast cancer cells, MDA-MB-468. The cells were incubated with and without RB4 (10 μM) for 60 minutes, and then insonated by a continuous ultrasound (1 MHz, 1 W/cm$^2$) for 30 seconds. FIG. 2A shows the microscopic images of the cells after treatment with RB4 along, ultrasound (US) alone, or RB4 plus US. As shown in FIG. 2A, significant damage was observed in cells treated with the RB4 combined with US treatment. Round detached cells and high amounts of debris were observed floating in the media. Little difference could be seen among the untreated, RB4 (alone) treated, and ultrasound (alone) treated groups. The treated cells were cultured for an additional day and then checked for viability, with the results shown in the bar chart in FIG. 2B. Ultrasound alone or RB4 alone had a mild effect on the cell's viability (>80% viable), while the RB4 combined with ultrasound treatment killed over 90% of cells. Based on these observations, the cell killing was rapid, and appeared to involve a complete loss of membrane integrity. A similar sono-sensitivity of RB4 was observed with a second cell line HT1080, fibrosarcoma, which resulted in 95% of the cells killed. RB4 is non-toxic to cells at the test concentration; its $IC_{50}$ to MDA-MB-468 and HT-1080 was 71 and 157 µM, respectively.

Figure 2C:
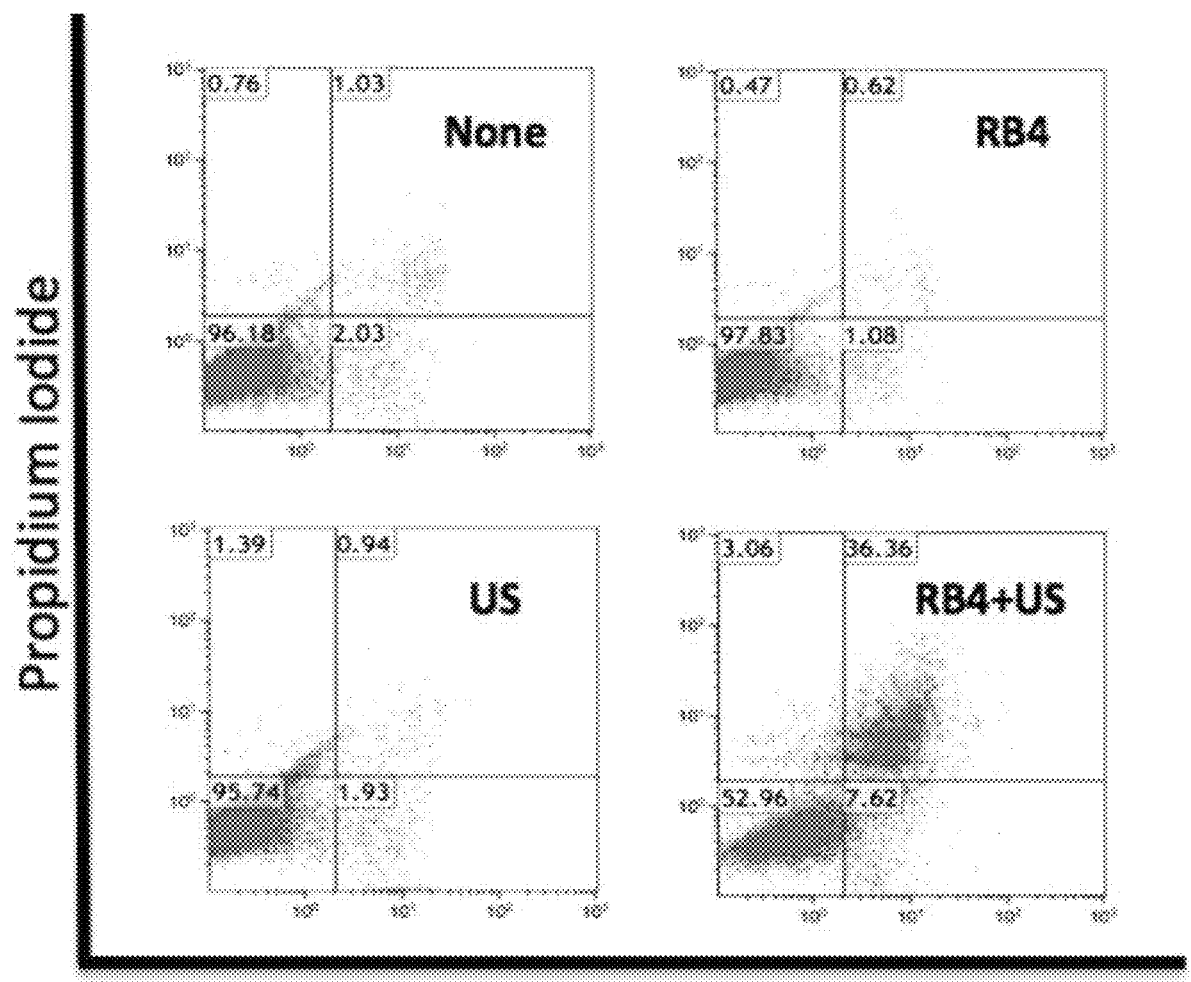

The cell death process was studied by staining the treated cells with apoptosis and necrosis dyes, annexin V and propidium iodide (PI), respectively. As shown by the FACS analysis plot in FIG. 2C, one day after treatment, RB4-treated or US-treated cells were similar to the untreated group, mostly healthy. However, a high percentage of the cells treated with the RB4-US combination was annexin/PI double positive (36%), plus a small fraction of annexin positive (8%) or PI positive (3%) cells. The actual dead cell population was larger than indicated in the FACS analysis plot in FIG. 2C because the fragments of the lysed cells could not be spun down during preparation.

Figure 2D:
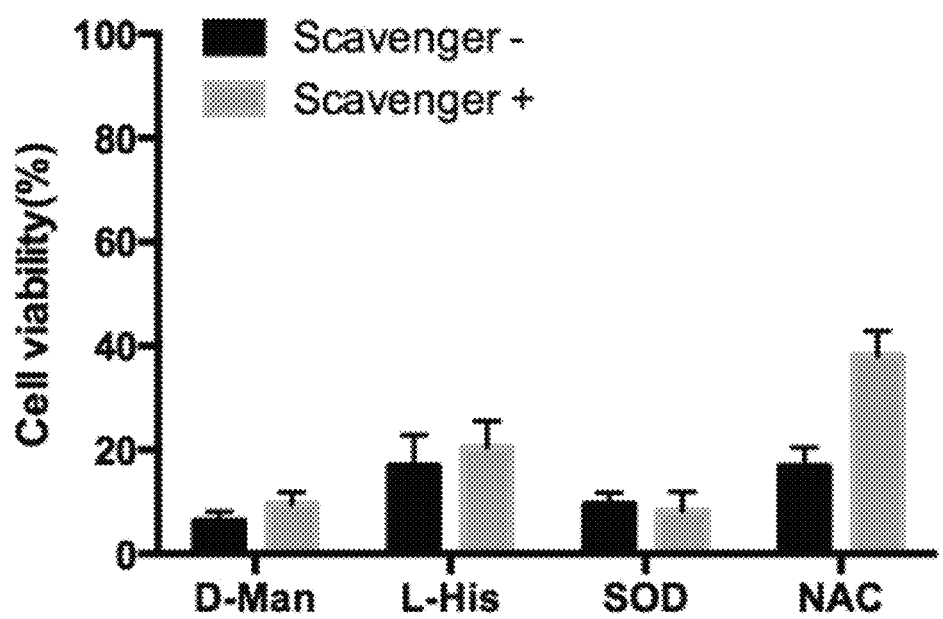

The majority of the reported sonosensitizers used in sonodynamic therapy are known to be photosensitizers or are derived from photosensitizers. Yet, RB4 is not a photosensitive molecule. The photon theory of sonodynamic therapy might not be applicable in RB4. To study the mechanism of action, a quantitative fluorescence dichloro-dihydro-fluorescein diacetate (DCFH-DA) assay was used to measure the ROS generation. Freshly prepared DCFH and RB4 solutions were insonated with different ultrasound powers. However, the absorption measurement indicated that the ROS level of RB4 solution was not significantly different from the background level of the DCFH solution, which indicates that insonated RB4 did not generate ROS in solution. The possible generation of ROS RB4 was then checked in MDA-MD-468 cells in the presence of various ROS scavengers, L-histidine (L-His) for singlet oxygen plus hydroxyl radicals, D-mannitol (D-Man) for hydroxyl radicals, superoxide dismutase (SOD) for superoxide radicals, and N-acetyl cysteine (NAC) for hydroxyl radicals plus hydrogen peroxide. As shown by the cell viability vs. scavenger plot in FIG. 2D, among all of the tested scavengers, none, with the exception of NAC, showed any protective effects. NAC was only able to rescue a small fraction (~20%) of cells from the RB4 and ultrasound combination treatments. These results suggest that hydrogen peroxide may only partially participate in cell toxicity, possibly as a side effect of cell lysis freeing it from intracellular compartments, rather than its direct generation by ultrasound. The majority of cells were killed through other mechanisms.

Based on these differences in mechanism studies, it is herein concluded that RB4 SED is not a typical sonosensitizer used in sonodynamic therapy. It produces little ROS, but surprisingly kills cells almost instantly under insonation. The cell killing process is rapid, and appears to involve a complete loss of membrane integrity. The evidence suggests that RB4 acts as a membrane destabilizer, weakening the extracellular membrane by inserting itself into the membrane, and promoting the membrane lysis tendency. Assisted by an ultrasound pressure that oscillates between compression and expansion, the membrane bursts almost immediately.

Figures 3A, 3B:
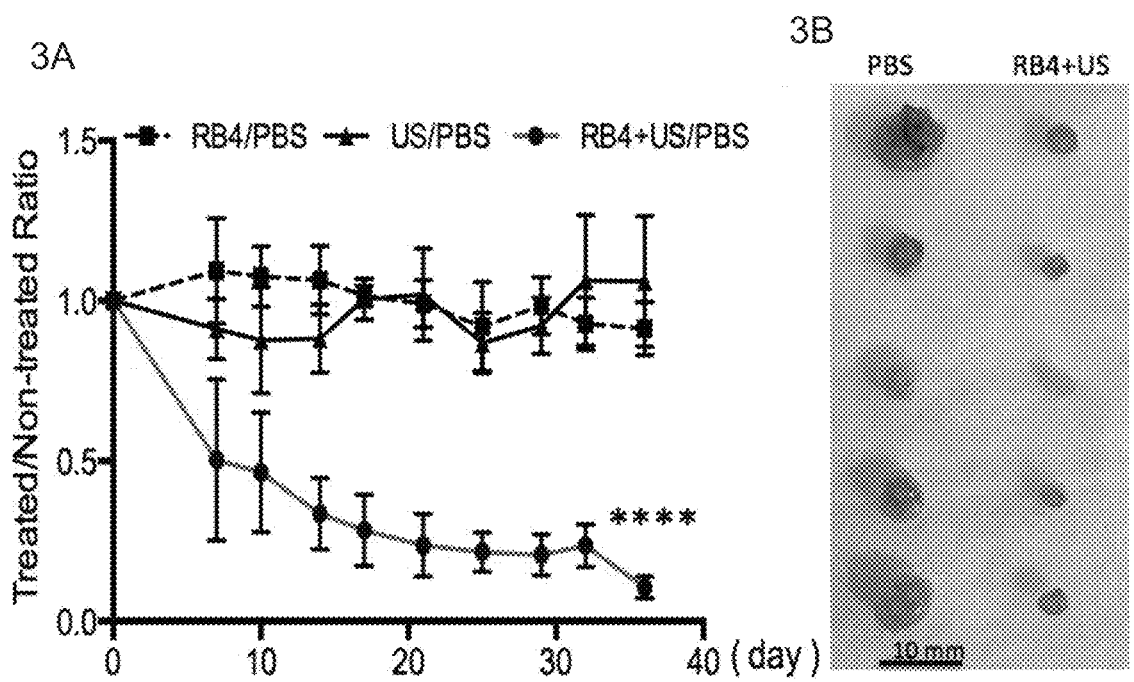
FIGS. 3A and 3B show an in vivo tumor inhibition effect of SMRT and controls.

The potential for tumor ablation using the RB4/ultrasound combination was evaluated in a triple negative MDA-MD-468 breast cancer xenograft model. To minimize the variation between animals, each animal was inoculated with two tumors. The treatment was then only applied to one of the tumors. The other tumor that had not received treatment served as an internal reference. The tumors were either treated with ultrasound alone (1 MHz, 1 W/cm², 3 min), RB4 alone (10 µM), or an RB4-ultrasound combination. For the experiments that required RB4, the cells ($5\times10^6$) were pre-incubated with RB4 (10 µM) for 1 day, and then subcutaneously inoculated into the flank. A handheld ultrasound transducer was placed on top of the injection site for 3 minutes with a continuous ultrasound (1 MHz, 1 W/cm²). This gentle ultrasound insonation did not cause visible negative effects to the contacted skin. The sono-membrane rupture therapy (SMRT) treatment effect was investigated non-invasively by measuring the tumor sizes twice a week up to 36 days, with the growth ratios of treated vs. untreated tumors plotted in FIG. 3A. As shown in FIG. 3A, there were no significant differences in tumor size among the untreated, RB4 (only) treated, and US (only) treated groups, which have similar growth rate ratios (≈1). In contrast, the RB4-assisted sonotherapeutic effect was significant throughout the tested period. As shown in FIG. 3A, the average size of tumors treated with the RB4-US combination was only about 20% of the control untreated tumor, FIG. 3B show's representative images of the excised tumors. The data clearly demonstrates that growth inhibition occurred only with the combination of RB4 and ultrasound. RB4 alone or ultrasound alone provided no appreciable inhibition effect. These long-term inhibition effects further demonstrate that the RB4-US combination provides anew effective way to ablate tumors.

Figure 4A:
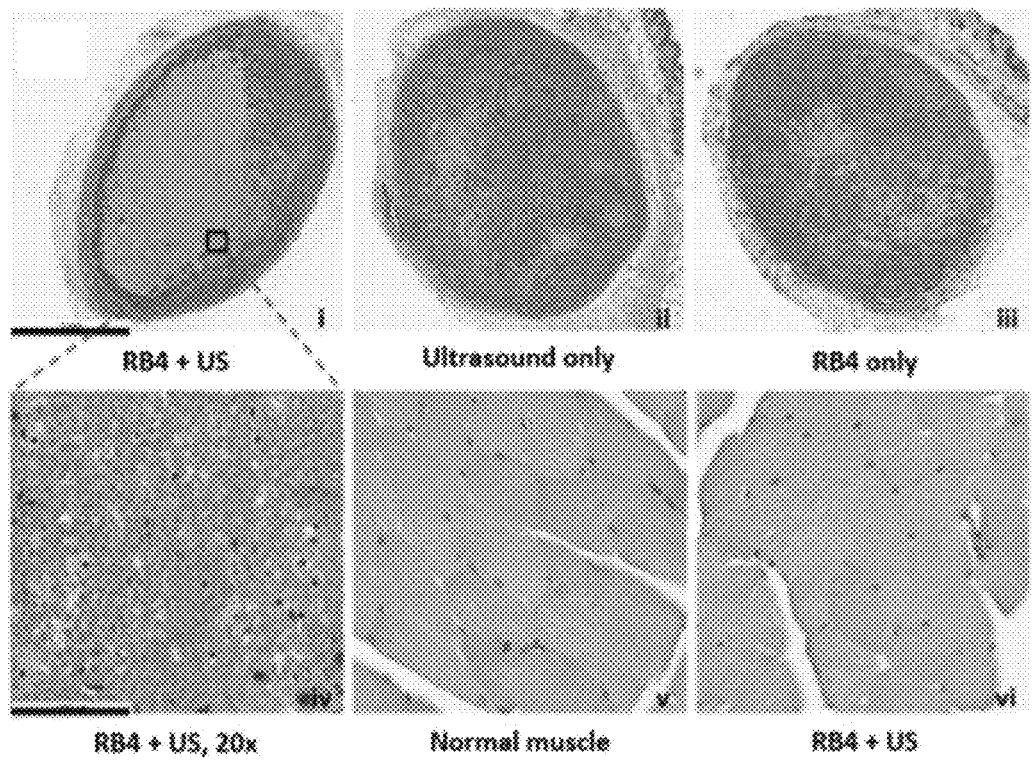
FIGS. 4A and 4B show an SMRT effect in the MDA-MB468 xenograft tumor model. RB4 (50 μl, 10 μM) was injected directly into the tumor and followed by a local insonation (1 MHz, 1 W/cm$^2$, 3 min). Treated and control tumors were excised two days later for pathological analysis. The same RB4/US treatment was applied to the thigh muscle as another control.
Figure 4B:
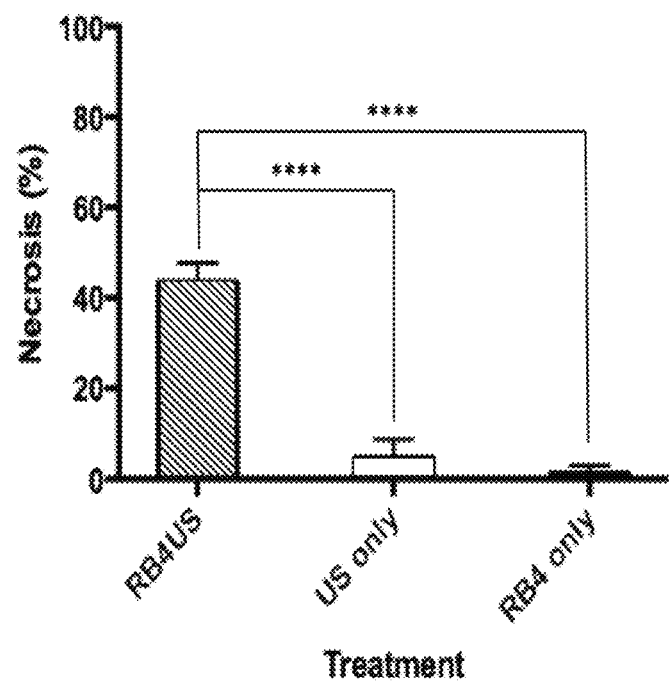

In view of this encouraging result using RB4, the RB4-US effect was further tested by direct intratumoral injection when tumors were about 4-5 mm in size. RB4 (50 µL, 10 µM) was injected directly into the tumor and followed by a local insonation (1 MHz, 1 W/cm², 3 minutes). Two days after treatment, the tumors were excised, sectioned, and checked for cell death by microscope visualization. The microscope images of the tumors are shown in FIG. 4A. As shown by panels (i) and (iv) in FIG. 4A, pathological microscopic analysis showed a large necrotic area (~40%) caused by the RB4 and ultrasound combination treatment. Importantly, when the same treatment was applied to normal muscle tissue, no damaged cells were found, as shown in panels (v) and (vi) in FIG. 4A. As shown in panels (ii) and (iii) in FIG. 4A, and similar to the PBS treated group, little tissue damage was observed with either ultrasound alone or RB4 alone in vivo. Both pre-treatment and direct intratumoral injection experiments support the clinical potential of low energy ultrasound induced tissue ablation.

The above results indicate that the RB4/ultrasound combination therapy was selective between tumor and muscle. It is known that cancer cells are at least 70% softer than healthy cells. Although the exact composition difference and role of the softness in cancer cells is still obscure, it has been suggested to be a factor in driving tumor metastasis (Fraldi M et al., *J. R. Soc. Interface.* 2015 Oct. 6; 12(111): 20150656). A frequency-based hypothesis for mechanically targeting and selectively attacking cancer cells). The intrusion of the bulky RB4 might weaken the cancer cell's plasma membrane, and then promote the ultrasound induced membrane lysis tendency. The healthy cells, which are much stiffer, may resist the insertion of RB4 and are less prone to ultrasound oscillation. This cell membrane selectivity further makes the SMRT method unique, safe, and effective.

In this study, a new low-intensity ultrasound assisted SMRT method has herein been demonstrated with a Rose Bengal derivative, RB4. RB4 alone does not lyse the plasma membrane. However, RB4 has herein been shown to cause membrane rupture when used together with an ultrasound wave of low intensity, and the cells with broken plasma membrane die nearly instantly. The frequency and intensity of the ultrasound are all within the medical imaging window; thus, the applied ultrasound is safe and causes no damage to healthy tissues. As the wavelength of ultrasound is too long to be absorbed by chemical bonds, it would not interact directly with SED to induce any chemical reactions. The cell death is thus likely a result of the physical oscillation. Instead of targeting the traditional therapeutic targets, such as pathways, receptors, enzymes, or genes, the above described SMRT method advantageously acts on the cell membrane. The treatment is substantially safe, since it requires no toxic ingredients or high-energy exposure. The treatment is also specific because it requires the combination of SED and ultrasound. Since the method does not act on the typical therapeutic targets, it could also overcome many existing drug resistance issues. Membranes, compared to other biomolecules, are less prone to mutation.

While there have been shown and described what are at present considered the preferred embodiments of the invention, those skilled in the art may make various changes and modifications which remain within the scope of the invention defined by the appended claims.

What is claimed is:

1. A method for ablating cancerous tissue in a subject, the method comprising incorporating a sound excitable compound into said cancerous tissue followed by exposure of said cancerous tissue to low-intensity ultrasound having an intensity of no more than 5 W/cm², said sound excitable compound having the following structure:

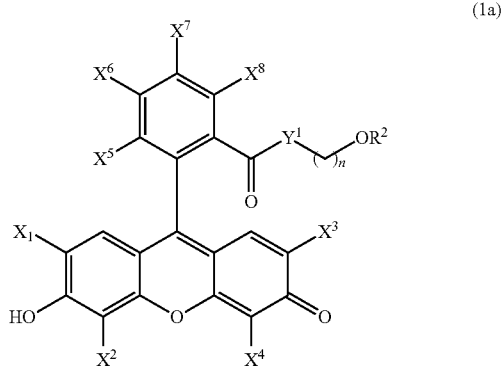

(1a)

wherein:
$X^1$, $X^2$, $X^3$, and $X^4$ are each independently selected from iodine and bromine atoms;
$X^5$, $X^6$, $X^7$, and $X^8$ are each independently selected from hydrogen atom, chlorine, bromine, and iodine atoms;
$Y^1$ is an —O—, —NR'—, or —CR'2-linker, wherein R' is independently selected from hydrogen atom and methyl;
$R^2$ is selected from hydrogen atom (H) and alkyl groups containing one to three carbon atoms; and
n is an integer of 1-12;
wherein said Formula (1a) includes pharmaceutically acceptable salts and solvates of the compounds embraced by Formula (1a).

2. The method of claim 1, wherein said sound excitable compound inserts within the cell membrane of cells in said cancerous tissue before said cancerous tissue is exposed to low-intensity ultrasound.

3. The method of claim 1, wherein said low-intensity ultrasound has an intensity of less than 5 W/cm².

4. The method of claim 1, wherein said low-intensity ultrasound has an intensity of no more than 2 W/cm².

5. The method of claim 1, wherein said low-intensity ultrasound has an intensity of no more than 1 W/cm².

6. The method of claim 1, wherein said cancerous tissue is in a breast.

7. The method of claim 1, wherein said sound excitable compound is dissolved in a pharmaceutically acceptable carrier.

8. The method of claim 1, wherein $X^1$, $X^2$, $X^3$, and $X^4$ are selected from iodine and bromine atoms.

9. The method of claim 1, wherein $Y^1$ is an —NR'— linker, wherein R' is selected from hydrogen atom and methyl.

10. The method of claim 1, wherein $X^1$, $X^2$, $X^3$, and $X^4$ are iodine atoms, and $Y^1$ is an —NR'— linker, wherein R' is selected from hydrogen atom and methyl.

11. The method of claim 1, wherein $X^1$, $X^2$, $X^3$, and $X^4$ are iodine atoms.

12. The method of claim 1, wherein $Y^1$ is an —NR'— linker, wherein R' is selected from hydrogen atom and methyl.

13. The method of claim 1, wherein $R^2$ is H.

14. The method of claim 1, wherein $X^1$, $X^2$, $X^3$, and $X^4$ are iodine atoms, and $Y^1$ is an —NR'— linker, wherein R' is selected from hydrogen atom and methyl.

15. The method of claim 14, wherein $R^2$ is H.

16. The method of claim 1, wherein said compound has the following structure:

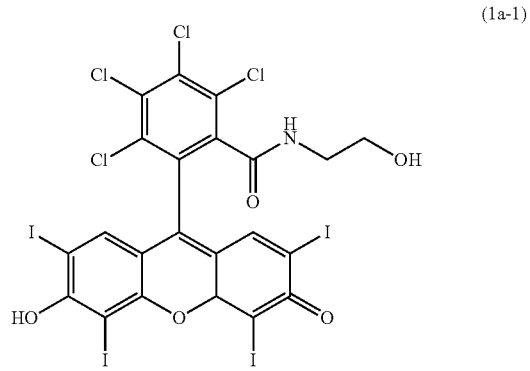

(1a-1)

and wherein said Formula (1a-1) includes pharmaceutically acceptable salts and solvates of the compounds embraced by Formula (1a-1).

* * * * *